United States Patent [19]

Nishimura et al.

[11] 3,961,041
[45] June 1, 1976

[54] EFFERVESCENT ENTERIC COATED L-DOPA FORMULATION AND METHOD OF USING THE SAME

[75] Inventors: Kenji Nishimura; Mikio Arai; Kunihiro Sasahara; Takashi Nitanai, all of Tokyo, Japan

[73] Assignee: Interx Research Corporation, Lawrence, Kans.

[22] Filed: Apr. 10, 1975

[21] Appl. No.: 566,745

[30] Foreign Application Priority Data
Nov. 14, 1974 Japan............................ 49-131304

[52] U.S. Cl.................................. 424/35; 424/44; 424/177
[51] Int. Cl.² ...................... A61K 9/22; A61K 9/46; A61K 9/30
[58] Field of Search........................ 424/35, 44, 177

[56] References Cited
UNITED STATES PATENTS

| | | | |
|---|---|---|---|
| 3,131,123 | 4/1964 | Masquelier | 424/35 |
| 3,891,696 | 6/1975 | Bodor et al. | 424/177 X |

FOREIGN PATENTS OR APPLICATIONS 2,116,256   8/1972   France

OTHER PUBLICATIONS

Sandler, M. et al. Lancet Feb. 16, 1974 pp. 238–240 Variation of Levodopa Metabolism with Gastrointestinal Absorption Site.
Eckstein, B. et al. Lancet Feb. 24, 1973 pp. 431–432 Sustained-Release Levodopa in Parkinsonism.
Curzon, G. et al. Lancet Apr. 7, 1973 p. 781 Sustained-Release Levodopa in Parkinsonism.
Voller, G. W. et al. Acta Neurol Scand 50(3): 391–393 (1974) Efficacy of and Possible Differences in Tolerance to L-DOPA Tablets with Different Rates of Release of the Active Substance.

*Primary Examiner*—Shep K. Rose
*Attorney, Agent, or Firm*—Charles N. Blitzer

[57] ABSTRACT

Therapeutic levels of L-DOPA are achieved by orally administering a pharmaceutical effervescent-enteric coated tablet comprising:
  a. a member selected from the group consisting of L-DOPA or a derivative thereof capable of enzymatically cleaving and reverting to L-DOPA in vivo,
  b. a non-toxic pharmaceutically acceptable inert diluent,
  c. a non-toxic pharmaceutically acceptable carbon dioxide releasing agent,
  d. a non-toxic pharmaceutically acceptable effervescing agent, and
  e. a non-toxic pharmaceutically acceptable enteric coating.

This composition is extremely useful in the treatment of Parkinsonism. When administered to warm-blooded animals (e.g., humans), superior therapeutic blood levels of L-DOPA are observed over that normally observed with conventional enteric coated formulations.

8 Claims, 1 Drawing Figure

EFFERVESCENT ENTERIC COATED L-DOPA FORMULATION AND METHOD OF USING THE SAME

BACKGROUND OF THE INVENTION

1. Field of the Invention

The present invention is directed to L-DOPA (3,4-dihydroxy-L-phenylalanine) and more particularly, the present invention is directed to a novel effervescent-enteric coated formulation containing L-DOPA or any derivative thereof, capable of enzymatically cleaving and releasing (reverting to) L-DOPA in vivo, in warmblooded animals, e.g., humans.

2. Description of the Prior Art

L-DOPA is the drug of choice in the treatment of Parkinson's Disease. It is reported, however, that this drug is only therapeutically effective when it is orally administered in massive doses, such as 2 to 3 grams per day or even as much as 8 grams per day, depending upon the seriousness of the disease. It is also known that therapeutic results can be obtained by administering 50 to 100 mg per day of the drug via intravenous injections. On the other hand, L-DOPA causes marked side effects when such massive dosing is administered. As such, some patients cannot realize thereapeusis because the side effects of L-DOPA eliminate therapeutic responses from the patient.

As a result of the above side effects observed when administering L-DOPA, at least one approach to eliminating the same has been established, i.e., essentially, inhibiting the direct action of the drug on the stomach wall. Normally, two reasons are given for not orally administering L-DOPA in massive doses:

1. L-DOPA is unstable in the gastrointestinal tract, especially in the stomach, and
2. L-DOPA is poorly absorbed from the gastrointestinal tract.

As for (1), it has been confirmed that the decomposition of L-DOPA in the stomach is remarkable as shown in numerous reports in the past. As for reason (2), however, the present inventors have clarified, after much experimentation, that the absorption of L-DOPA is not appreciably different when the drug is administered orally as compared to when it is administered intravenously. Moreover, the present inventors have observed that L-DOPA is almost completely absorbed from the gastrointestinal tract.

Based on the foregoing, a standard enteric dosage form of L-DOPA was developed and clinically tested by the present inventors as well as many other researchers. However, the results of such testing showed that while the side effects of L-DOPA were reduced, the therapeutic effect of the drug was markedly inferior. That is, with the standard enteric coated formulation, the side effects (nausea and vomiting) normally encountered with L-DOPA administration could be overcome; however, therapeusis could not be achieved.

After various further studies, the present inventors determined that the optimum absorption site of L-DOPA is located in the small intestine, especially in the upper part thereof, and that a conventional enteric coated tablet containing L-DOPA will not completely disintegrate at the upper part of the small intestine. As a result, optimum absorption of the drug is totally incomplete.

Meanwhile, it is known that L-DOPA is apt to undergo decarboxylation via decarboxylase enzymes which exist in the intestine. Such decarboxylation converts L-DOPA into dopamine, a metabolite of L-DOPA in the course of the absorption process in the intestine. It is also known that dopamine does not permeate the blood-brain barrier, and, therefore, does not have any therapeutic effect in the treatment of Parkinson's Disease. For this reason, it was necessary to make every effort to inhibit the conversion of L-DOPA into dopamine in the intestinal tract.

Because of the above determinations, the expected total absorption of L-DOPA to achieve a substantial therapeutic effect cannot be obtained via formulating L-DOPA in a conventional enteric coated tablet.

It is obvious, based on the foregoing, that a great need exists for an orally administrable L-DOPA formulation which will permit L-DOPA or any derivative thereof capable of reverting to L-DOPA in vivo to achieve a substantial therapeutic effect without initiating accompanying side effects.

SUMMARY OF THE INVENTION

Considering the above, the present inventors have developed an enteric coated L-DOPA formulation which is characterized as (1) not decomposed in the stomach, (2) not subject to decarboxylation in the intestine, and (3) highly absorbed through the gastrointestinal tract. Essentially, the present invention concerns delivering L-DOPA or any derivative thereof capable of enzymatically cleaving and reverting to L-DOPA in vivo via an effervescent-enteric coated tablet. By using such a formulation, the effervescent nature thereof permits total disintegration and release of L-DOPA all at once, when L-DOPA or any suitable derivative thereof, as characterized above, reaches the intestine. That is, the effervescent-enteric coated preparation permits L-DOPA to enter the small intestine without undergoing decomposition in the stomach after oral administration.

Subsequently, the enteric film dissolves rapidly in the upper part of the small intestine, i.e., the optimum absorption site therein. Upon contact of the effervescent-enteric coated preparation with the intestinal juice, a large amount of L-DOPA or any suitable derivative thereof as characterized above will be released therefrom, whereby it will be dissolved in the intestinal juice all at once. The dissolved L-DOPA is absorbed as it is from the optimum absorption site and conversion of L-DOPA into dopamine is quite remarkably inhibited. As a result, the maximum blood-concentration of unchanged L-DOPA, which is obtainable by using such preparation, is three to seven times higher than that reached when administering L-DOPA via a conventional enteric-coated preparation. Moreover, the total absorption of L-DOPA (as unchanged L-DOPA) is substantially improved.

It is quite surprising that the conversion of L-DOPA into dopamine normally caused by decarboxylation in the intestine is markedly inhibited by administering L-DOPA in an effervescent-enteric coated preparation. The present inventors feel that such results stem from the so-called saturation phenomenon of enzymatic reaction which is brought about by disintegrating and releasing L-DOPA all at once. With the results obtained according to this invention, it has become possible to employ L-DOPA or any suitable derivative thereof as characterized above in a much smaller dose as compared with the massive doses required to date for coventional oral administration. Moreover, with the effervescent-enteric coated formulation described herein, a noticeable decrease in side effects is observed.

DETAILED DESCRIPTION OF THE INVENTION

Figure 1:
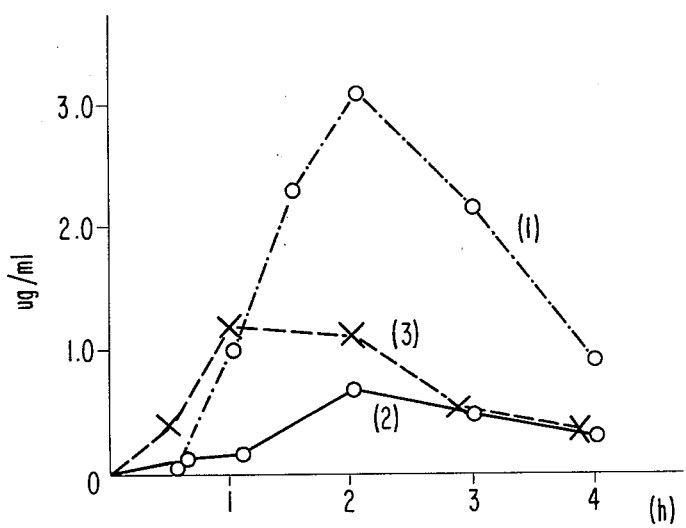

As for the enteric coating material to be employed in the instant invention, any conventional enteric coating is suitable. For example, without limitation, cellulose acetate phthalate (CAP) and hydroxypropylmethylcellulose phthalate (HPMCP), etc. are suitable. Other enteric coatings suitable for the purpose of the instant invention can be found in the text entitled "REMINGTON'S PHARMACEUTICAL SCIENCES," Fourteenth Edition (1970), pages 1689–1691. It is preferable to employ those enteric coatings which dissolve in a pH range of from 4.5 to 5.0 in order that the L-DOPA or derivative thereof can be disintegrated at the optimum absorption site in the small intestine. Illustrative but not limitative examples of such materials are HPMCP-50 and HPMCP-45, respectively.

As for the effervescing composition, naturally, a non-toxic pharmaceutically acceptable carbon dioxide releasing agent in combination with a non-toxic pharmaceutically acceptable effervescing agent is required. As for the former, illustrative but not limitative examples are: tartaric acid, citric acid, citric anhydride, phthalic acid, etc. Additional exemplary effervescing agents can be found in "REMINGTON'S PHARMACEUTICAL SCIENCES" pages 802, 803 and 1462 as identified above. As for the latter ingredient, any conventional pharmaceutically acceptable carbon dioxide releasing agent is suitable. For example, sodium bicarbonate or any equivalent thereof will suffice. Additional exemplary carbon dioxide releasing agents can also be found in "REMINGTON'S PHARMACEUTICAL SCIENCES", pages 802, 803 and 1462 as identified above.

In addition to L-DOPA, numerous L-DOPA derivatives which are known to enzymatically "cleave" and revert back to L-DOPA in vivo will suffice for purposes of the instant invention. The following derivatives are therefore illustrative but not limitative of all the derivatives operable for applicants' purposes. All of the following derivatives (and others meeting the above requirement) are disclosed in U.S. Pat. No. 3,891,696, the subject matter of which is incorporated herein by reference.

I. 3,4-diacylated derivatives of L-dopa and the salts thereof 1. 3,4-diacetyloxy-L-phenylalanine hydrochloride

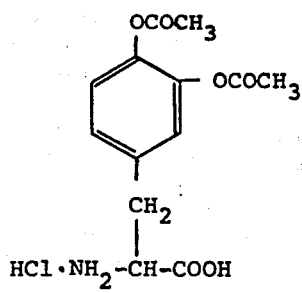

2. 3,4-dipivalyloxy-L-phenylalanine perchlorate

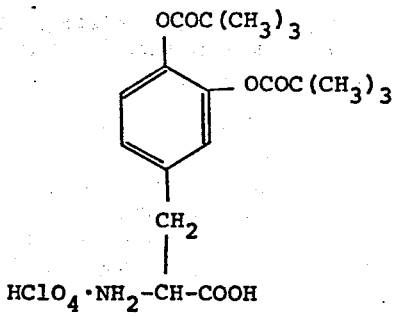

II. Carboxyl esters of L-dopa or those of the 3,4-diacylated derivatives of L-dopa, and the salts thereof 1. 3,4-dihydroxy-L-phenylalanine methyl ester hydrochloride

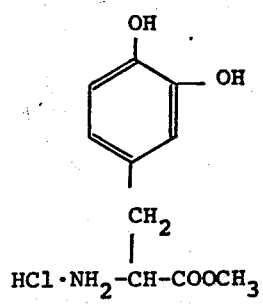

2. 3,4-diacetyloxy-L-phenylalanine methyl ester hydrochloride

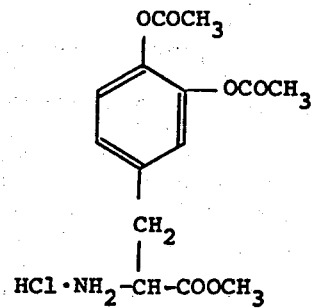

3. 3,4-dihydroxy-L-phenylalanine benzyl ester hydrochloride

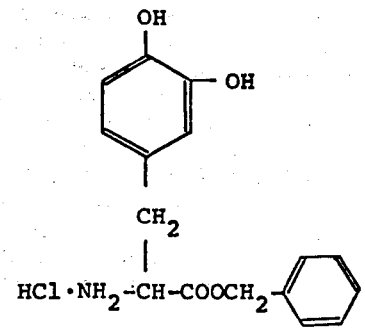

4. 3,4-diacetyloxy-L-phenylalanine benzyl ester hydrochloride

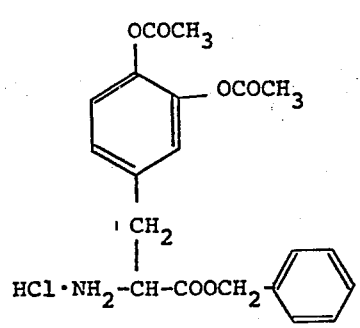

5. glycyl-3,4-diacetyloxy-L-phenylalanine methyl ester hydrochloride

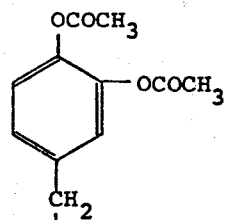

III. Enamine derivatives of L-dopa or those of the 3,4-diacylated derivatives of L-dopa pivalyloxymethyl
1. 3,4-dipivalyloxy-N(1-methyl-2-acetylvinyl)-L-phenylalanine pivalyloxymetyl ester

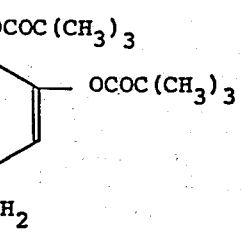

2. 3,4-dipivalyloxy-N(1-methyl-2-acetylvinyl)-L-phenylalanine potassium salt

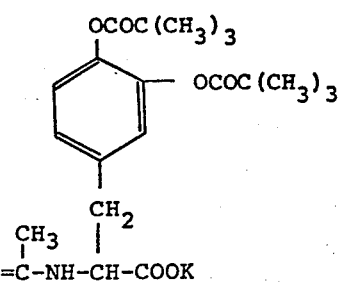

3. 3,4-diacetyloxy-N(1-methyl-2-acetylvinyl)-L-phenylalanine potassium salt

IV. Amine derivatives of L-dopa or those of the 3,4-diacylated derivatives of L-dopa
1. N-formyl-3,4-dipivalyloxy-L-phenylalanine

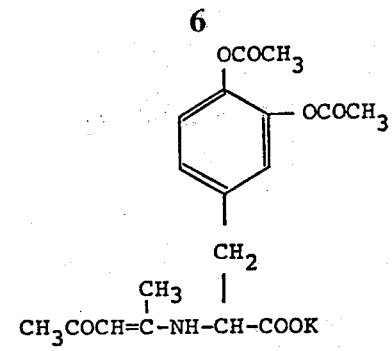

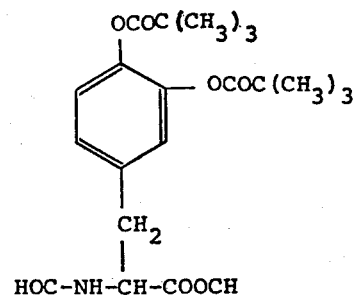

2. N-formyl-3,4-dipivalyloxy-L-phenylalanine-pivalyloxymethyl ester

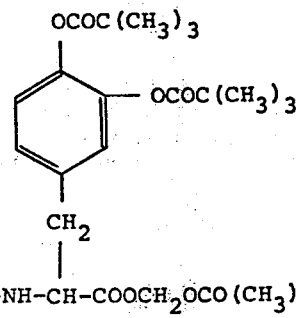

3. N-formyl-3,4-diacetyloxy-L-phenylalanine

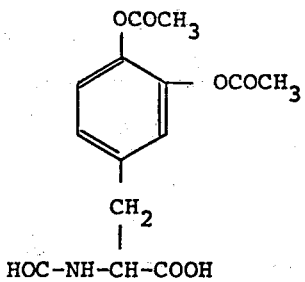

4. N-formyl-3,4-diacetyloxy-L-phenylalanine potassium salt

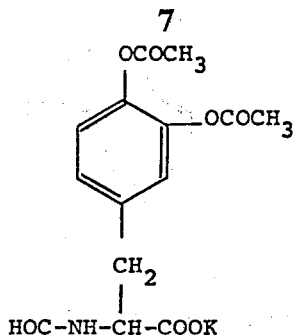

5. glycyl-3,4-diacetyloxy-L-phenylalanine hydrochloride

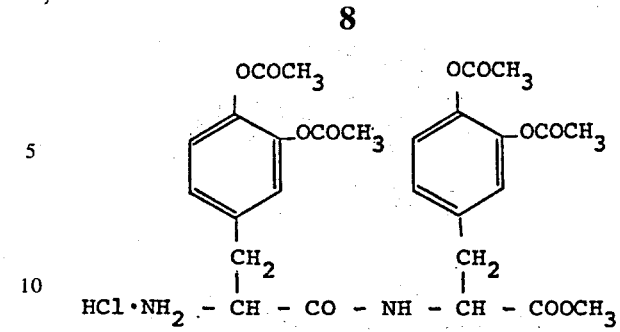

3. 3,4-diacetyloxy-L-phenylalanyl-3,4-diacetyloxy-L-phenylalanine benzyl ester hydrochloride

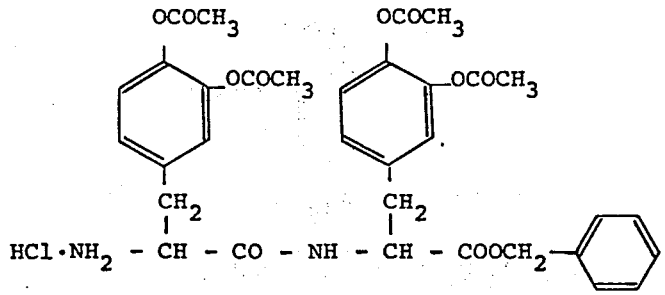

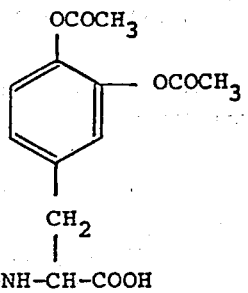

6. 3,4-diacetyloxy-L-phenylalanylglycine hydrochloride

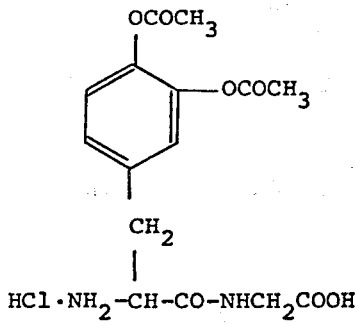

V. Dipeptides of L-dopa 1. 3,4-dihydroxy-L-phenylalanyl-3,4-dihydroxy-L-phenyl-alanine hydrochloride

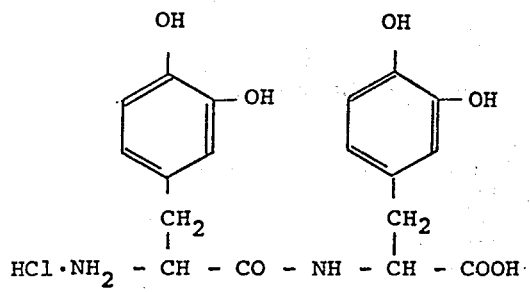

2. 3,4-diacetyloxy-L-phenylalanyl-3,4-diacetyloxy-L-phenylalanine methyl ester hydrochloride The tablets of this invention may be slightly more fragile than conventional tablet preparations from a tablet-strength standpoint, since the former contains an effervescent composition. For this reason, it may be desirable to incorporate therein a dry binding agent such as microcrystalline cellulose. In addition, the incorporation of microcrystalline cellulose has the advantage of improving the immediate release of L-DOPA or any suitable derivative thereof as characterized above at the optimum absorption site. Naturally, other additives such as stabilizers, disintegrators, and lubricants can also be added, if desired. In this regard, reference is made to "REMINGTON'S PHARMACEUTICAL SCIENCES" noted earlier.

Without further elaboration, it is believed that one of ordinary skill in the art can, using the preceding description, utilize the present invention to its fullest extent. As such, the following preferred specific embodiments are, therefore, to be construed as merely illustrative, and not limitative of the remainder of the specification and claims in any way whatsoever.

EXAMPLE I

The following composition is formulated into an effervescent-enteric coated tablet weighing 264 mg per tablet.

| | |
|---|---|
| L-DOPA | 100 mg |
| Tartaric Acid | 50 |
| Sodium Bicarbonate | 56 |
| Carboxymethylcellulose | 20 |
| Microcrystalline cellulose | 30 |
| Talc | 6 |
| Magnesium Stearate | 2 |
| Total | 264 mg |

Onto this tablet, there is sprayed a solution of 10% w/w (HPMCP-50 dissolved in a 1:1 (by weight) mixture of methylene chloride and ethanol. The tablet is coated until the total weight thereof increases by 10% w/w (based on the uncoated tablet). Thus is obtained the final product.

The results of the dissolution test for the preparation of the thus obtained tablet are shown in Table I-A. The dissolution test applys the disintegration test disclosed in the Japanese Pharmacopoeia and Solution No. II defined in the Japanese Pharmacopoeia is employed as the dissolution medium.

EXAMPLE II

The following composition is formulated into an effervescent coated tablet weighing 276 mg per tablet.

| | |
|---|---|
| L-DOPA | 100 mg |
| Citric Anhydride | 62 |
| Sodium Bicarbonate | 56 |
| Carboxymethylcellulose | 20 |
| Microcrystalline cellulose | 30 |
| Talc | 6 |
| Magnesium Stearate | 2 |
| Total | 276 mg |

This tablet is coated in the same manner as the tablet of Example I to give the final effervescent-enteric coated product. The results of the dissolution test for the preparation thus prepared are shown in Table I-B.

A tablet prepared in the same manner as the tablet in Example I is sprayed with a solution of 8% (w/w) cellulose acetate phthalate and 2% (w/w) polyethylene glycol 6000 dissolved in acetone. The tablet is coated until the total weight thereof increases by 10% (w/w) based on the uncoated tablet. The results of the dissolution test for this preparation are shown in Table I-C.

EXAMPLE IV

Reference Example

The method described in Example I is repeated but lactose is employed instead of sodium bicarbonate and tartaric acid. The results of the dissolution test for the preparation thus obtained are shown in Table I-D.

TABLE
RESULTS OF THE DISSOLUTION TEST

| | Tested Preparations | | | |
|---|---|---|---|---|
| | A | B | C | D |
| Time elapsed before beginning of dissolution (minute) | 4 | 4.5 | 6.5 | 5 |
| Time required to dissolute 90% of L-DOPA after beginning of dissolution (minute) | 2 | 2 | 2.5 | >60 |

As shown in Table I, it is obvious that the time required to dissolve the preparations of the instant invention (A, B, and C) are remarkably shortened in comparison with that required for the control preparation (D). Moreover, the momentary-release property of the former preparations in the intestine is quite superior to that of the latter.

EXAMPLE V

Blood-Concentration Test

The preparation obtained according to the instant invention and the controlled preparation were orally administered to Beagle dogs and the blood-concentrations thereof were measured.

FIG. 1 accompanying the instant application shows that the average blood-concentration of L-DOPA in Beagle dogs, which was measured by administering 100 mg of L-DOPA to each of the six Beagle dogs tested, separating out the L-DOPA in the plasma with an ion-exchange resin after deproteinization, and then fluorometrically determining the blood-concentration via the THI method (trihydroxyindole method). In FIG. 1, (1) represents the blood-concentration given by administering the effervescent-enteric coated tablet of Example I of this application, (2) represents that given by administering the standard enteric coated tablet of Example IV, and (3) represents that given by administering a commercially available L-DOPA capsule (non-enteric coated). It is apparent from FIG. 1 that the L-DOPA preparation of the present invention (effervescent) exhibits a much higher blood-concentration and a far larger area under the blood-concentration curve (1). This is indicative of superior L-DOPA absorption over conventional L-DOPA preparations.

From the foregoing description, one of ordinary skill in the art can easily ascertain the essential characteristics of the instant invention, and without departing from the spirit and scope thereof, can make various changes and modifications of the invention to adapt it to various usages and conditions. As such, these changes and modifications are properly, equitably, and intended to be, within the full range of equivalence of the following claims.

What we claim is:

1. A pharmaceutical effervescent enteric-coated tablet for oral administration to a warm-blooded animal which permits release and absorption of L-DOPA in the area of the upper portion of the small intestine thereof comprising a tableted admixture of:

a. a member selected from the group consisting of L-DOPA, 3,4-diacetyloxy-L-phenylalanine or a pharmaceutically acceptable acid addition salt thereof, 3,4-dipivalyloxy-L-phenylalanine or a pharmaceutically acceptable acid addition salt thereof, 3,4-dihydroxy-L-phenylalanine methyl ester or a pharmaceutically acceptable acid addition salt thereof, 3,4-diacetyloxy-L-phenylalanine methyl ester or a pharmaceutically acceptable acid addition salt thereof, 3,4-dihydroxy-L-phenylalanine benzyl ester or a pharmaceutically acceptable acid addition salt thereof, 3,4-diacetyloxy-L-phenylalanine benzyl ester or a pharmaceutically acceptable acid addition salt thereof, glycyl-3,4-diacetyloxy-L-phenylalanine methyl ester or a pharmaceutically acceptable acid addition salt thereof, 3,4-dipivalyloxy-N(1-methyl-2-acetylvinyl)-L-phenylalanine pivalyloxy methyl ester, the alkali metal salt of 3,4-dipivalyloxy-N(1-methyl-2-acetylvinyl)-L-phenylalanine, the alkali metal salt of 3,4-diacetyloxy-N(1-methyl-2-acetylvinyl)-L-phenylalanine, N-formyl-3,4-dipivalyloxy-L-phenylalanine, N-formyl-3,4-dipivalyloxy-L-phenylalanine-pivalyloxymethyl ester, N-formyl-3,4-diacetyloxy-L-phenylalanine, the alkali metal salt of N-formyl-3,4-diacetyloxy-L-phenylalanine, glycyl-3,4-diacetyloxy-L-phenylalanine or a pharmaceutically acceptable acid addition salt thereof, 3,4-diacetyloxy-L-phenylalanylglycine or a pharmaceutically acceptable acid addition salt thereof, 3,4-dihydroxy-L-phenylalanyl-3,4-dihydroxy-L-phenylalanine or a pharmaceutically acceptable acid addition salt thereof, 3,4-diacetyloxy-L- phenylalanyl-3,4-diacetyloxy-L-phenylalanine methyl ester or a pharmaceutically acceptable acid addition salt thereof, and 3,4-diacetyloxy-L-phenylalanyl-3,4-diacetyloxy-L-phenylalanine benzyl ester or a pharmaceutically acceptable acid addition salt thereof,
b. a non-toxic pharmaceutically acceptable inert diluent,
c. a non-toxic pharmaceutically acceptable effervescent couple acid and base, and
d. a non-toxic pharmaceutically acceptable enteric coating over said entire tableted admixture.

2. The tablet of claim 1, wherein said diluent is talc.

3. The tablet of claim 1, wherein said effervescing agent is a member selected from the group consisting of tartaric acid, citric acid, citric anhydride, and phthalic acid.

4. The tablet of claim 1, wherein said carbon dioxide releasing agent is sodium bicarbonate.

5. The tablet of claim 1, wherein said enteric coating is a member selected from the group consisting of cellulose acetate phthalate and hydroxypropylmethylcellulose phthalate.

6. The tablet of claim 5, wherein said hydroxypropylmethylcellulose phthalate is a member selected from the group consisting of hydroxypropylmethylcellulose phthalate-50 and hydroxypropylmethylcellulose phthalate-45.

7. The tablet of claim 1, further comprising microcrystalline cellulose as a dry binding agent.

8. A method for orally inducing higher therapeutic blood levels of L-DOPA in a warm-blooded animal as compared to those blood levels obtained from administering conventional enteric-coated L-DOPA tablets to said animal comprising:

administering thereto, the tablet of claim 1.

* * * * *